United States Patent [19]

Schmitt et al.

[11] Patent Number: 5,309,777

[45] Date of Patent: May 10, 1994

[54] MEASURING INSTRUMENT PARTICULARLY USEFUL FOR MEASURING WASTE GASES FROM HEATING INSTALLATIONS

[75] Inventors: Rudi Schmitt; Werner Schmitt, both of Ludwigshafen, Fed. Rep. of Germany

[73] Assignee: S & G Schmitt Messgeraetebau GmbH, Ludwigshafen, Fed. Rep. of Germany

[21] Appl. No.: 750,947

[22] Filed: Aug. 28, 1991

[30] Foreign Application Priority Data

Sep. 1, 1990 [DE] Fed. Rep. of Germany ....... 4027715

[51] Int. Cl.$^5$ .................... G01D 7/00; G01D 3/08
[52] U.S. Cl. .................... 73/866.3; 364/431.01; 73/23.31; 374/143
[58] Field of Search ............ 73/1 G, 4 R, 23.2, 23.31, 73/31.04, 753, 714, 866.3, 866.1, 431; 374/142, 143, 163; 364/509, 510, 431.01

[56] References Cited

U.S. PATENT DOCUMENTS

| | | | |
|---|---|---|---|
| 3,313,160 | 4/1967 | Goldman | 73/866.1 |
| 3,322,938 | 5/1967 | Weiss | 364/510 X |
| 3,380,044 | 4/1968 | Mordwinkin | 73/866.1 |
| 4,171,637 | 10/1979 | Blanke | 73/118.1 |
| 4,175,427 | 11/1979 | Blanke | 73/118.1 |
| 4,423,487 | 12/1983 | Buckenham et al. | 73/112 X |
| 4,464,172 | 8/1984 | Lichtenstein | 128/13 |
| 4,485,666 | 12/1984 | Higgins et al. | 73/23.2 |
| 4,526,028 | 7/1985 | Hübner | 73/23.2 |
| 4,738,147 | 4/1988 | Tomlin | 73/23.2 X |
| 4,747,296 | 5/1988 | Feldon et al. | 73/753 X |
| 4,786,472 | 11/1988 | McConnell et al. | 73/23.31 X |
| 5,002,055 | 3/1991 | Merki et al. | 128/670 X |
| 5,091,863 | 2/1992 | Hungerford et al. | 73/863.01 X |

FOREIGN PATENT DOCUMENTS

| | | | |
|---|---|---|---|
| 47813 | 3/1982 | European Pat. Off. | 73/866.3 |
| 2730229 | 1/1979 | Fed. Rep. of Germany | 73/866.3 |
| 157301 | 9/1982 | Japan | 364/431.01 |
| 27208 | 2/1983 | Japan | 364/431.01 |
| 86602 | 5/1983 | Japan | 364/431.01 |
| 753709 | 9/1980 | U.S.S.R. | 364/510 |

OTHER PUBLICATIONS

"Passive Encoder for Range Knobs"; Bureau of Mines Information Circular/1983; IC 8939; First Available on Aug. 2, 1983; William H. Schiffbauer; pp. 1-8.

Primary Examiner—Tom Noland
Attorney, Agent, or Firm—Foley & Lardner

[57] ABSTRACT

The present invention relates to a measuring instrument, in particular for measuring waste gases from heating installations, comprising at least one sensor and pump arranged in a measuring channel, a microcomputer for controlling the measuring sequence and for processing the sensor signals, which is connected to an alphanumeric display device and two control elements, wherein one control element serves for paging in a selection menu, by which one menu item is displayed on the display device, and wherein the other control element serves to input in accordance with the menu item displayed.

15 Claims, 11 Drawing Sheets

<u>The three menus</u>

Concealed in the program are three menus, from which commands and functions can be selected as from a restaurant menu.

The interrelationships are evident from the following overview:

*) name of the instrument

MEASURING INSTRUMENT PARTICULARLY USEFUL FOR MEASURING WASTE GASES FROM HEATING INSTALLATIONS

BACKGROUND OF THE INVENTION

The invention relates to a measuring instrument which is useful for measuring waste gases from heating installations.

Various measuring instruments are known for measuring the waste gases from heating installations. However, these known instruments are quite complicated to handle and often quite heavy and large. Measuring instruments which operate with a computer are also known. However, in these instruments, the multiplicity of control elements requires intensive familiarization on the part of users with the measuring instruments.

SUMMARY OF THE INVENTION

It is therefore an object of the present invention to provide a measuring instrument which is simple to operate and can be transported easily to or at the place of use.

The measuring instrument according to the invention comprises at least one sensor and pump arranged in a measuring channel, a microcomputer for controlling the measuring sequence and for processing the sensor signals, and connected to the microcomputer an alphanumeric display device and two control elements, wherein one control element functions to page in a selection menu by which one menu item is displayed on the display device, and the other control element functions to input in accordance with the menu item displayed.

Further objects, features, and advantages of the present invention will become apparent from the detailed description of preferred embodiments that follows.

BRIEF DESCRIPTION OF THE DRAWINGS

FIG. 5 shows a flowchart of a subroutine and FIGS. 6A–6G, collectively referred to as FIG. 6, show a flowchart of a program for the microcomputer in the case of the measuring instrument according to FIG. 4.

DETAILED DESCRIPTION OF THE PREFERRED EMBODIMENTS

It is preferable that the control elements are push-buttons and that a further push-button is provided which is connected to an on/off switch.

Another preferred refinement consists in that the push-buttons for the control elements are arranged on the front side of the measuring instrument near one edge of the front side, which side also bears the display device. As a result, the measuring instrument can be held and operated with one hand. The risk of incorrect operation is reduced if the push-buttons for each control element are arranged within a depression, closer together than the push-button for the on/off switch is to the nearest control element.

Operation is further facilitated when the sequence of inputs and measurements to be performed by the operator is predetermined according to a program provided for the microcomputer and wherein inputs and measurements are only possible if they are meaningful after preceding inputs.

Another further development of the invention consists in providing a pressure sensor in the measuring channel. This makes possible a simple measurement of the stack draft. All that is required for this development is activation of the corresponding menu item and closing the outlet opening of the measuring channel.

According to another further development, a temperature sensor is provided and arranged in the measuring channel to measure different temperatures.

Illustrative embodiments of the invention are explained in greater detail with reference to the several figures in the drawing in which identical components are provided with the same reference numerals.

The measuring instrument (see FIGS. 1 and 2) according to the invention has a parallelepipedal casing 1. The front side contains a window 2 for a liquid-crystal display 3, by which alphanumeric characters can be displayed on two lines. In the vicinity of the right-hand edge of the front side there are two push-buttons 4 and 5, for operating the measuring instrument, and a further push-button 6, for switching the measuring instrument on and off. The push-buttons 4 and 5 are arranged relatively close together in a depression 7, whereas the push-button 6 is somewhat removed from the push-buttons 4 and 5, in a separate depression 8. The described arrangement of the push-buttons makes it possible to grasp the measuring instrument with the right hand and actuate the push-buttons with the thumb. An inadvertent switching-off of the measuring instrument is rendered difficult because of the greater distance of push-button 6 from 5 relative to the distance between push-buttons (4) and (5) and the separate depression for push-button (6).

Figure 1:
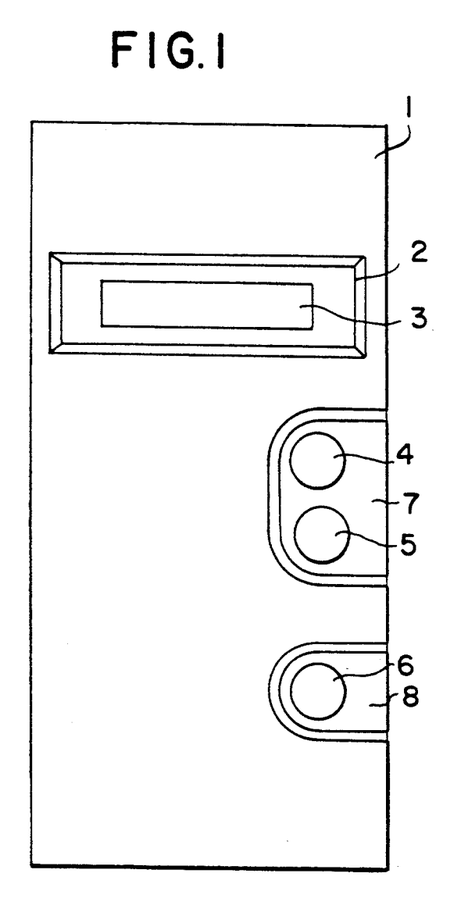
FIG. 1 shows a front view of the measuring instrument.
Figure 2:
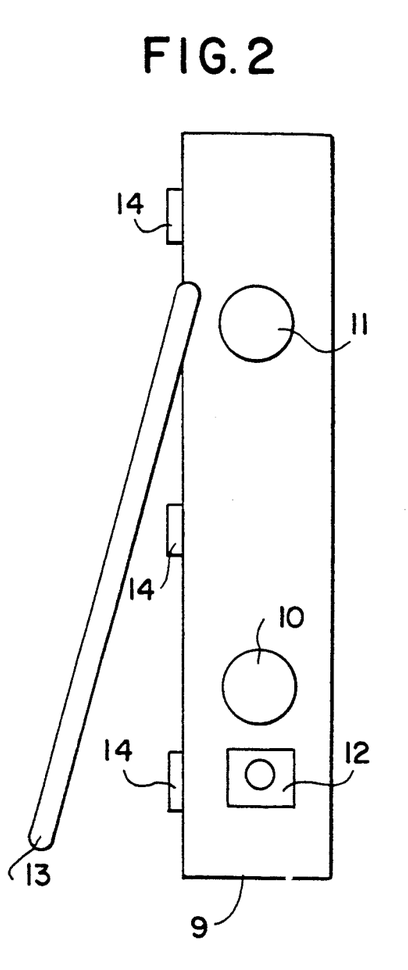
FIG. 2 shows a side view of the measuring instrument.

Provided on the left-hand side wall 9 are an intake opening 10 and an outlet opening 11 for the gas to be measured. In a measuring channel (not shown) there is a pump and sensors. The sensors include one electrochemical fuel cell for measuring oxygen, one for measuring carbon monoxide, optionally a temperature-dependent resistance element for measuring temperature and optionally a piezoresistive pressure transducer for measuring pressure. The output signals of the sensors are conditioned in a known manner, analog/digitally converted and fed to a microcomputer, in which, inter alia, programs are used for calibration of the individual sensors, for error compensation and for correcting possibly non-linear characteristics of the sensors.

Also provided on the left-hand side wall 9 is a connection 12 for a power supply unit, through which the built-in storage battery can be charged. Furthermore, the measuring instrument has a stirrup-shaped stand 13, which can be swung out from the area of the side wall. Via a multi-contact receptacle (not shown), which represents a standardized interface, for example a V24 interface, measurement data stored in the measuring instrument can be output, for example, to a personal computer. On the rear wall there are also magnetic strips 14 arranged, for fastening the measuring instrument, for example, to a boiler wall.

Apart from the processing of the sensor signals, already mentioned, additional functions are performed by the microcomputer by means of suitable programs. For example, after switching-on, a program for adjusting the measuring instrument is activated. This involves the oxygen measuring device being automatically calibrated to 20.9% by volume and the carbon monoxide device being automatically set to 0. The pressure measuring device, serving for draft measurement, is also adjusted to 0.

Figure 3:
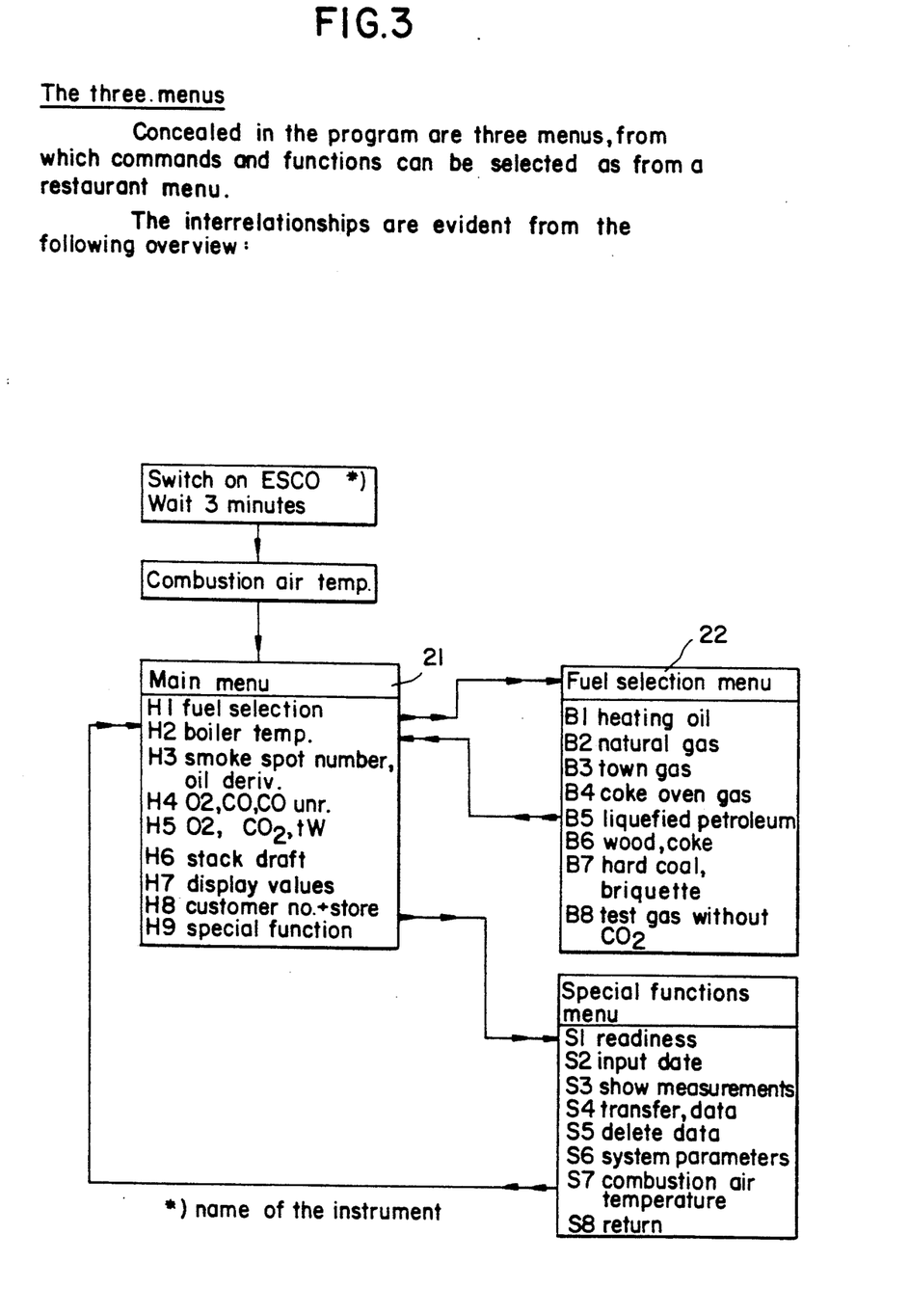
FIG. 3 shows a representation of the menu provided for operating the measuring instrument, from which commands and functions can be selected as from a restaurant menu.

The control operations required for operating the measuring instrument are explained with reference to FIG. 3. Once the adjusting program has run, the program of the microcomputer is in main menu 21. One of the menu items H1 to H9 of the main menu 21 can be viewed on the liquid-crystal display device, referred to from now on as LCD display. Once the adjusting program has run, initial menu item H1, "fuel selection" appears, since all other measurements depend on this selection. To select the fuel, the input button 5 is actuated, whereupon one of the items B1 to B6 of the fuel selection menu 22 appears on the LCD display. By repeated actuation of the menu button 4, the menu item B1 to B6 applicable for the respective fuel is selected and subsequently input with the input button 5. With the aid of the other menu items of the main menu 21, the measurements required for the selected fuel can be carried out.

The following further menu items have been found useful for the measuring instrument.

H2—boiler temperature,

H3—input of the three smoke spot numbers and oil derivatives in the case of HEL (heating oil extra light), H4—measurement and display of $O_2$, CO, CO unrarefied (waste gas path verification with multi-hole probe only in the case of gas), H5—measurement and display of $O_2$, $CO_2$, waste gas temperature (tw) (waste gas loss measurement with combined probe)

H6—stack draft measurement,

H7—display of all measured and calculated values as a check,

H8—input of customer number, and store, start of the next measurement.

If the input button 5 is actuated when item H9 "special function" in the main menu can be viewed, a special function menu 23 is called up, by which various special functions selected from menu items S1 to S7 can be called up. With menu item S8, the user is returned to the main menu 21.

Figure 4:
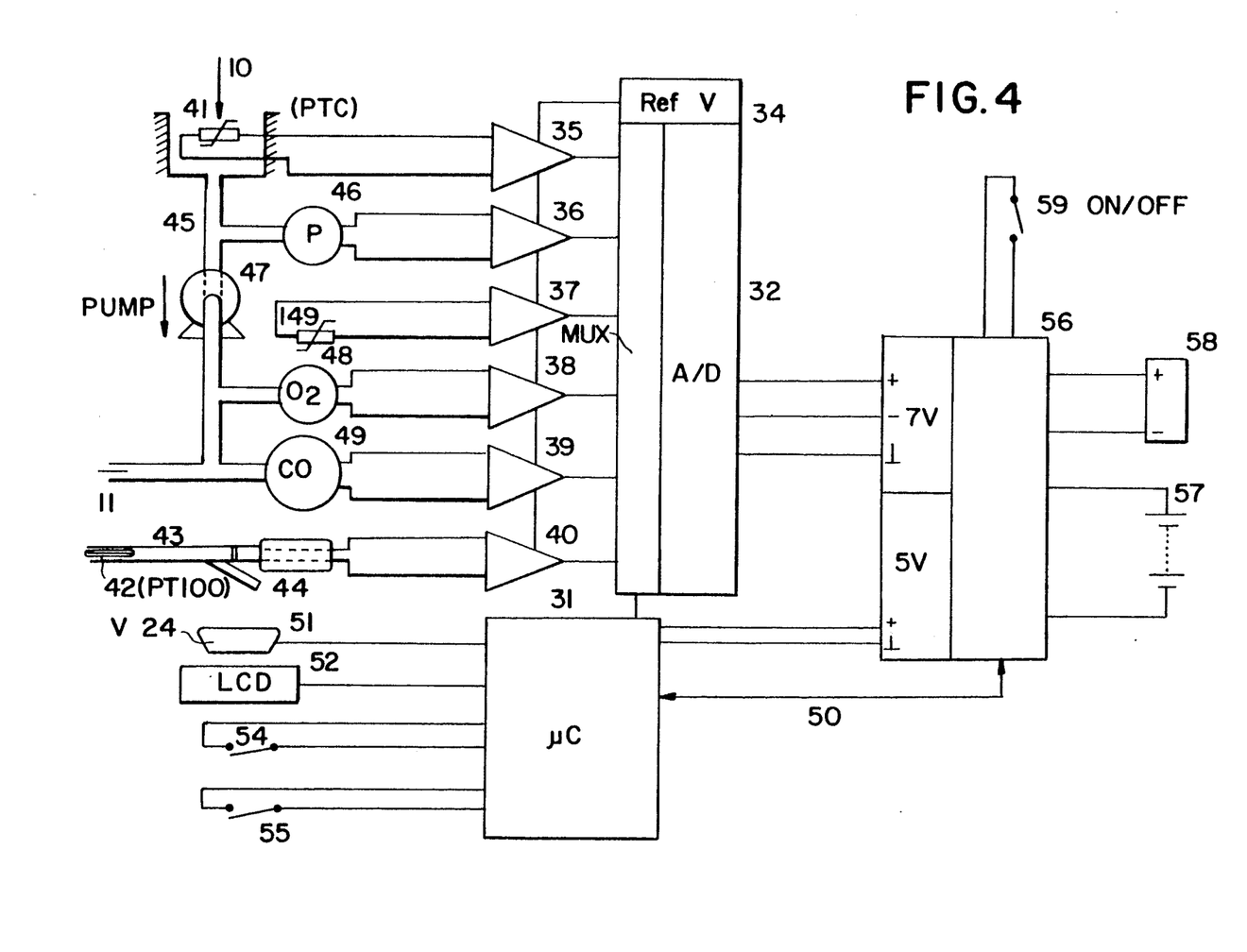
FIG. 4 shows a block diagram of a measuring instrument according to the invention.

FIG. 4 shows a block diagram of a measuring instrument according to the invention, in which a micro-computer 31 is connected in a known way to an analog/digital converter 32, upstream of which a multiplexer 33 is connected. The multiplexer 33 has six inputs for analog signals. The analog/digital converter 32 is assigned a reference voltage source 34, which is also in connection with amplifiers 35 to 40. These function for amplifying the voltages supplied by the sensors 41 to 46.

A first temperature sensor 41 is located within the intake opening 10 and functions to measure the ambient temperature. A second temperature sensor 42 is located at the end of a flexible probe 43, which is shown at the amplifier 40 because of the electrical connection with the latter, but can be fitted by a corresponding connector 44 into the intake opening.

A piezoelectric pressure sensor 46 is provided for measuring the pressure in the entry region of the measuring channel 45. A pump 47 pumps the gas to be measured from the intake opening 10 of the gas channel to the outlet opening 11. Since the pressure sensor 46 is arranged in the entry region, a simple measurement of the pressure, in particular of the stack draft pressure, is possible by calling up the appropriate menu item and closing the outlet opening 11.

Arranged elsewhere along the measuring channel 45 are sensors 48 and 49 for the measurement of oxygen and carbon monoxide, respectively. Suitable sensors in the form of electro-chemical fuel cells are commercially available. In order to compensate for the temperature dependence of the oxygen sensor 48, the temperature of the oxygen sensor 48 is measured with the aid of a third temperature sensor 149.

After appropriate amplification, the output signals of the sensors are converted with the aid of the multiplexer 33 and the analog/digital converter 32 into a digital multiplex signal, which is fed to the micro-computer 31. Also connected to suitable inputs/outputs of the microcomputer 31 are: a V24 interface 51, a liquid-crystal display 52 and contacts 54 and 55 of the push-buttons 4 and 5.

A power supply circuit 56 generates from the voltage of a storage battery 57 or from a direct voltage fed in at 58 an operating voltage of 5V for the micro-computer 31 and an operating voltage of 7V for the analog/digital converter 32 and the multiplexer 33. Also connected to the power supply circuit 56 are contacts 59 of the on-/off button 6. With the aid of the power supply circuit 56, the storage battery 57 can be charged by means of the direct voltage fed in at 58. The microcomputer 31 and power supply circuit 56 are connected to each other by a data line 50. For switching off the instrument, the position of the contacts 59 can be inquired into by the microcomputer 31. If the inquiry reveals that the push-button 6 has been actuated, the microcomputer 31 instigates the switching-off of the instrument via the data line 50. Depending on the operating state, this can take place immediately after button actuation or later, for example, after the measured data have been stored.

Figure 5:
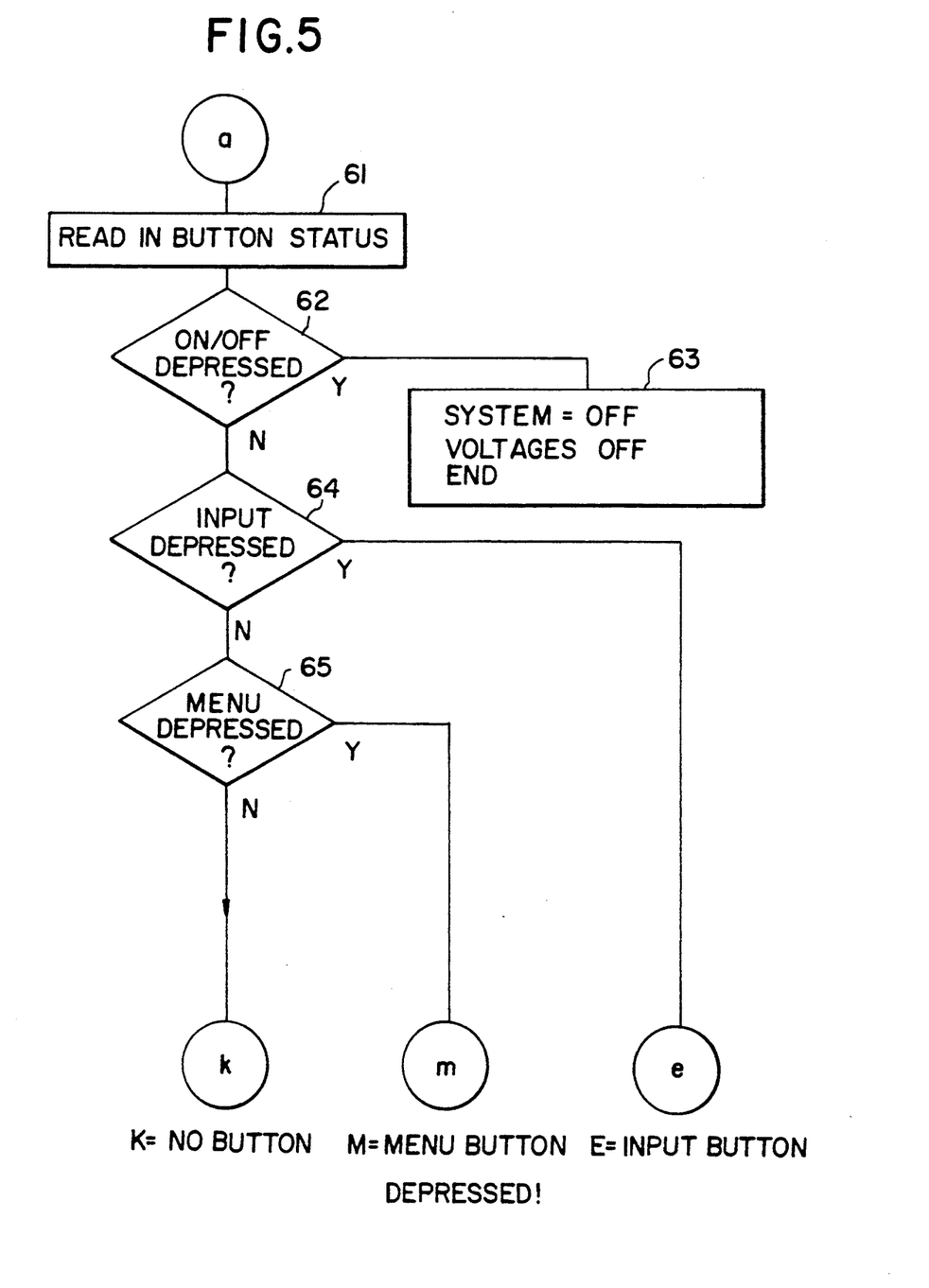
Figure 6A:
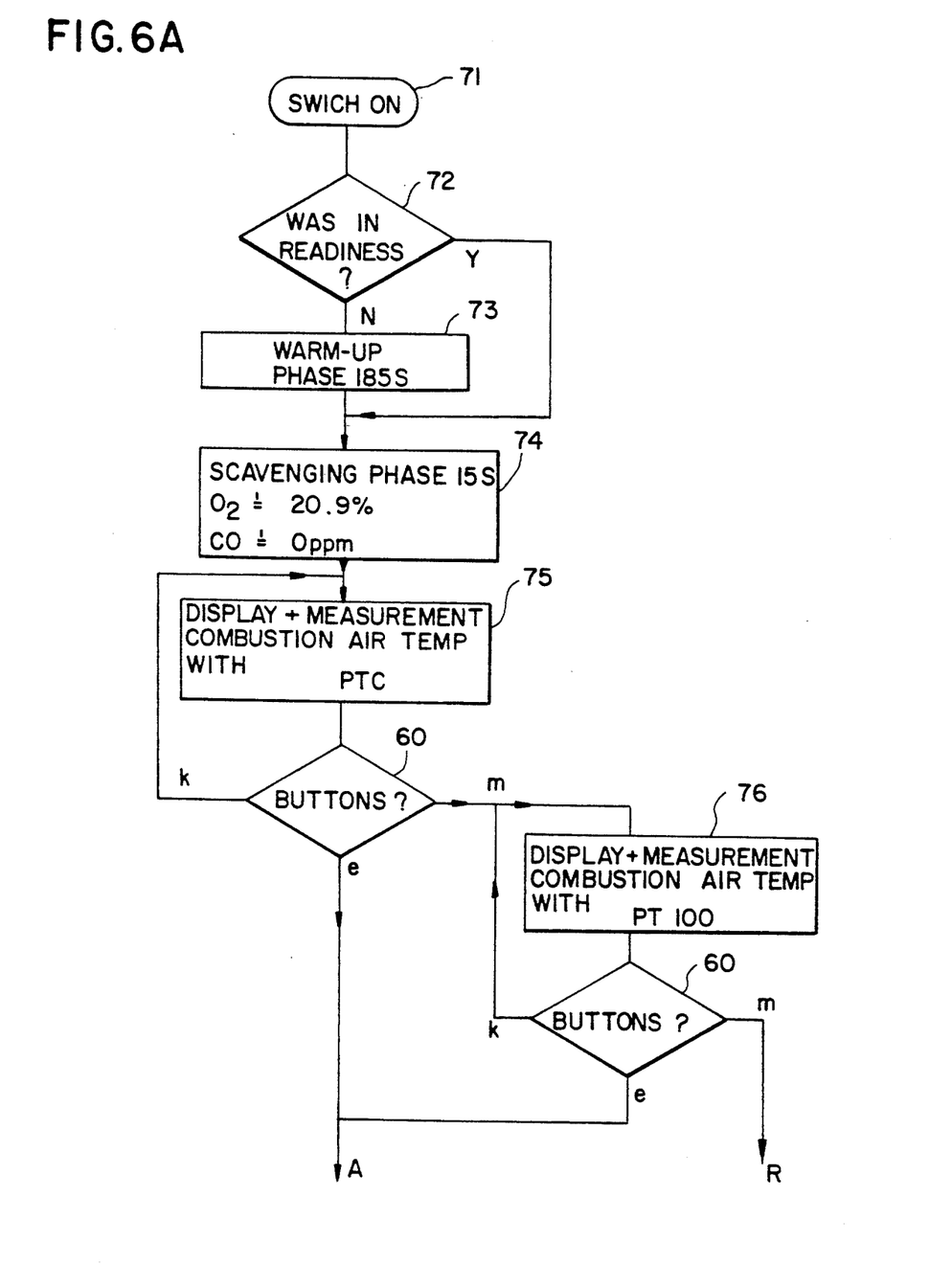
Figure 6B:
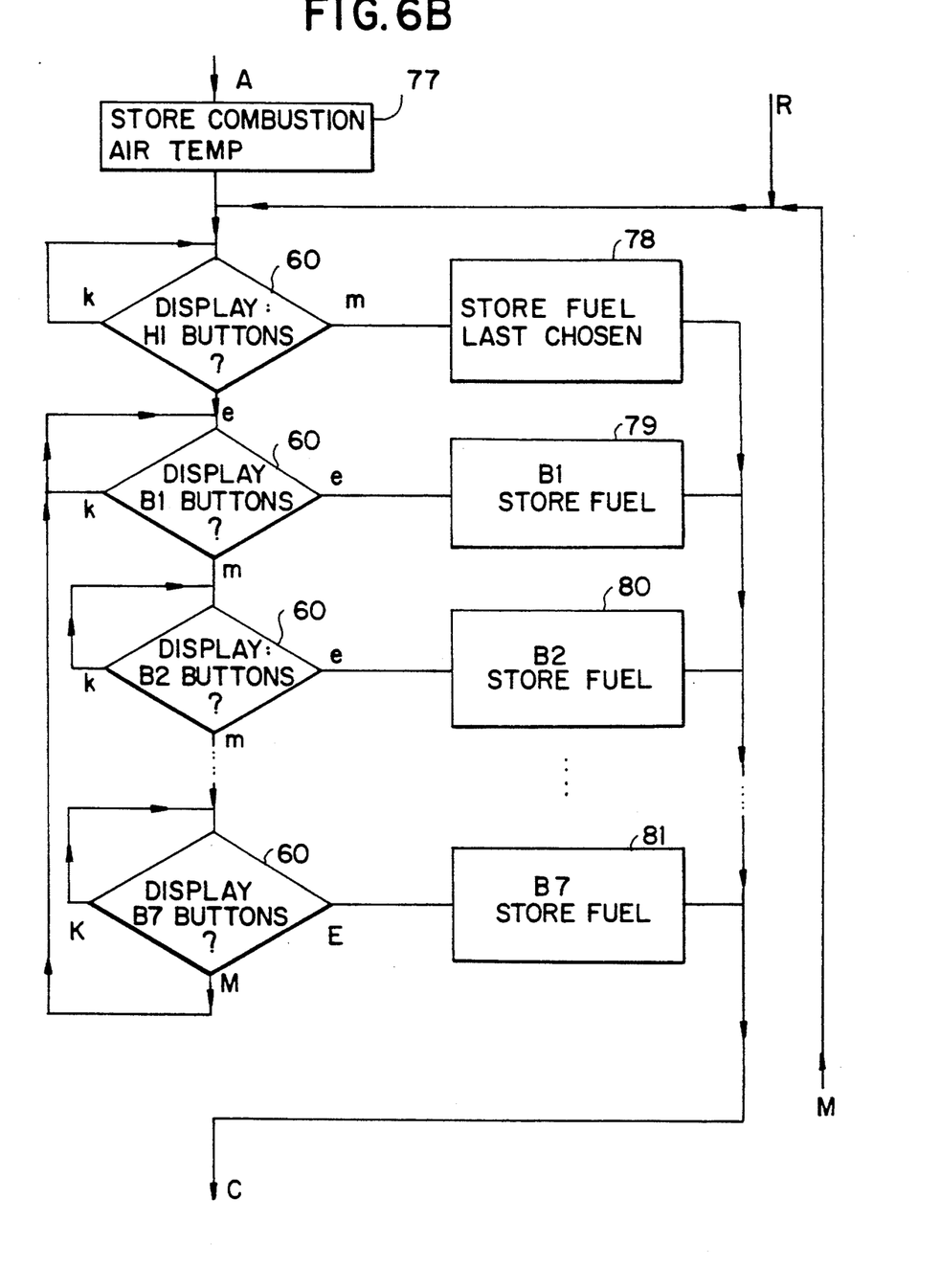
Figure 6C:
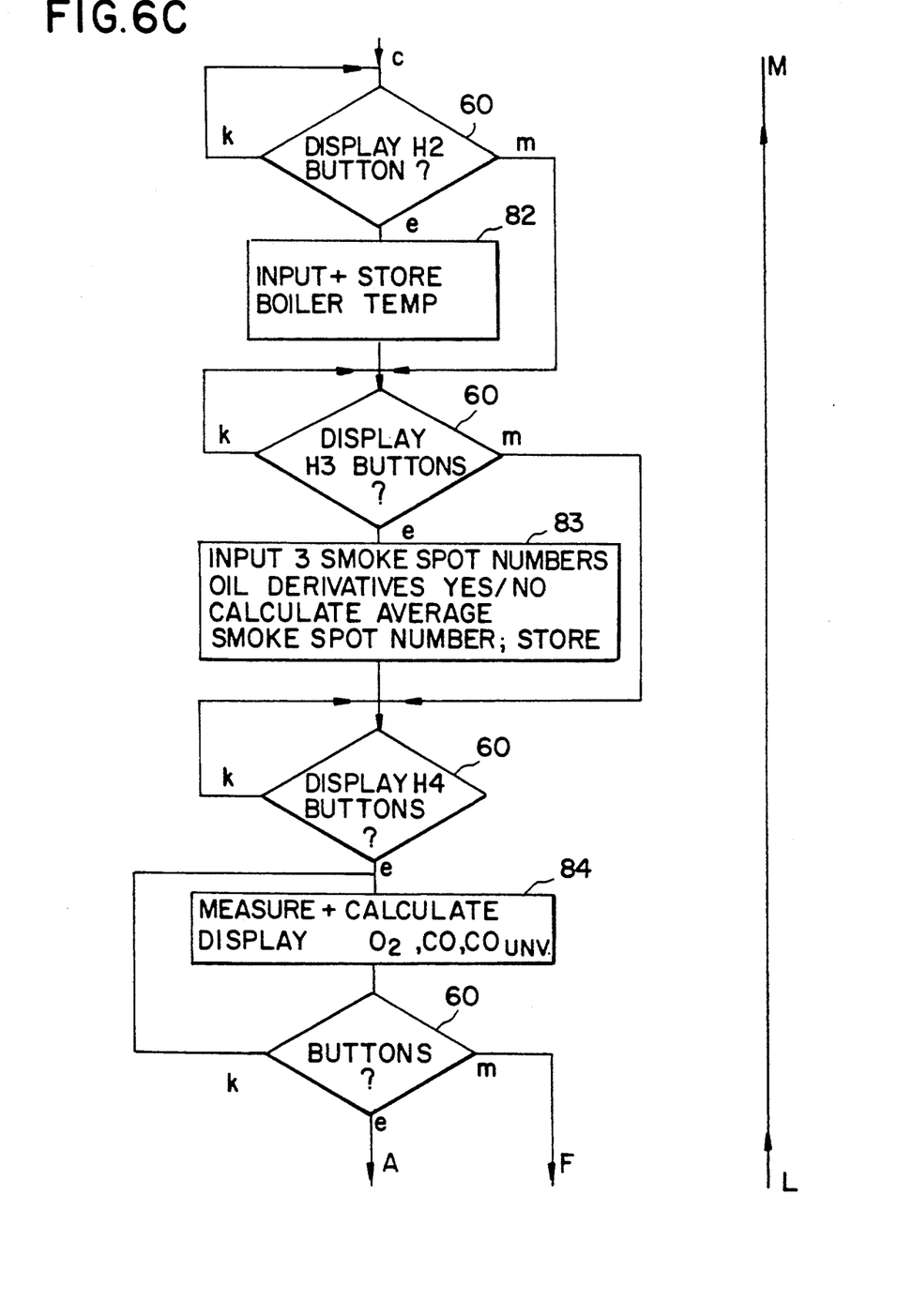
Figure 6D:
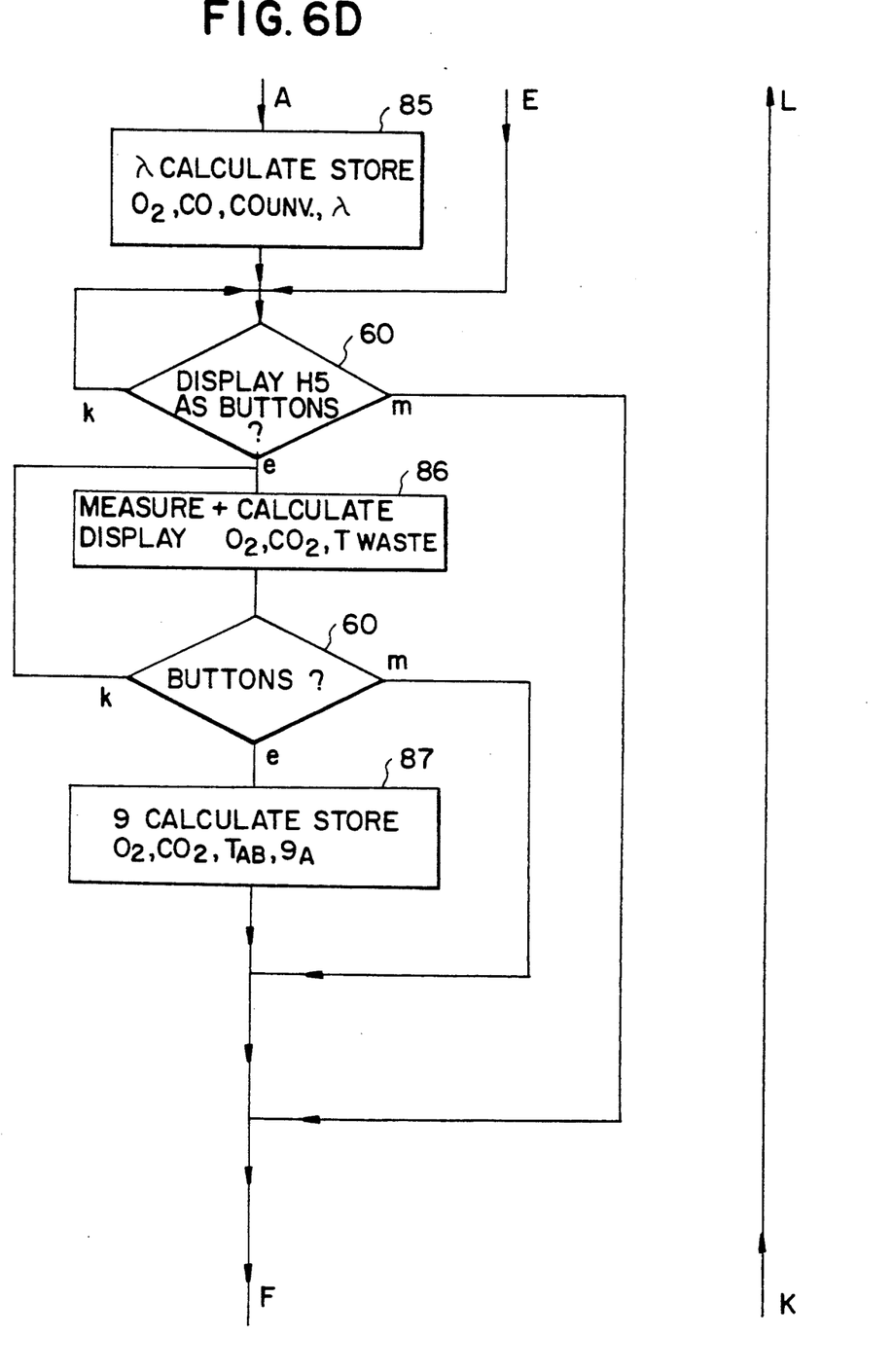
Figure 6E:
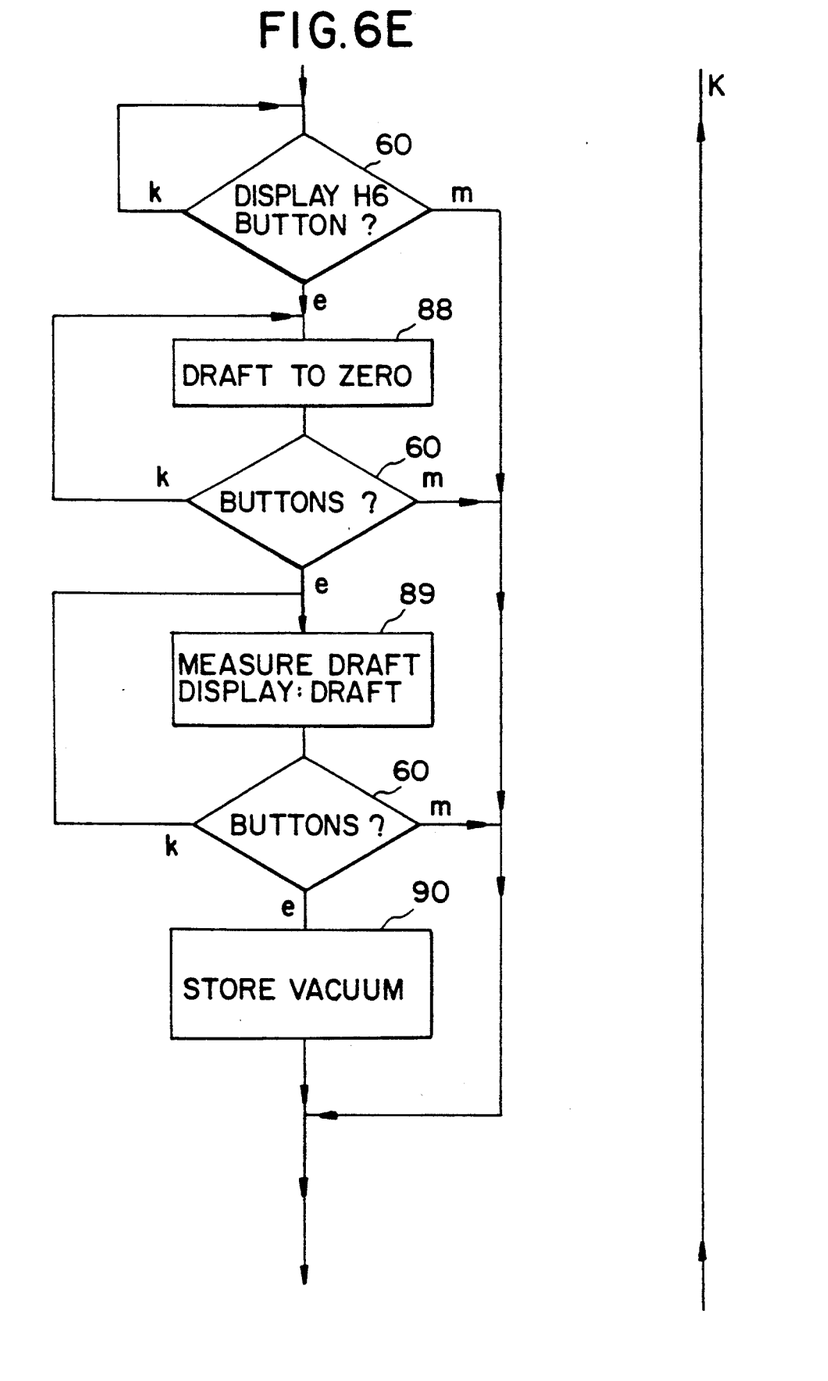
Figure 6F:
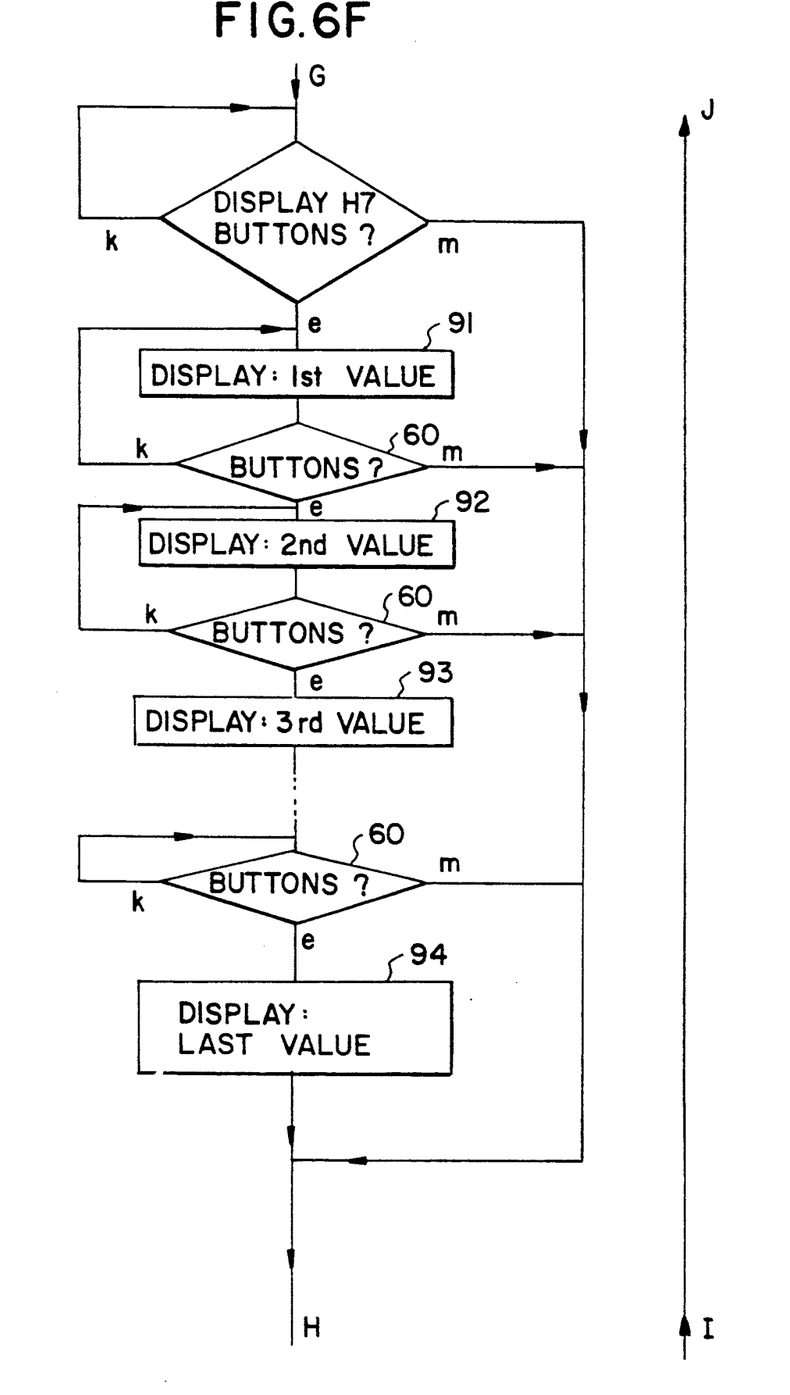
Figure 6G:
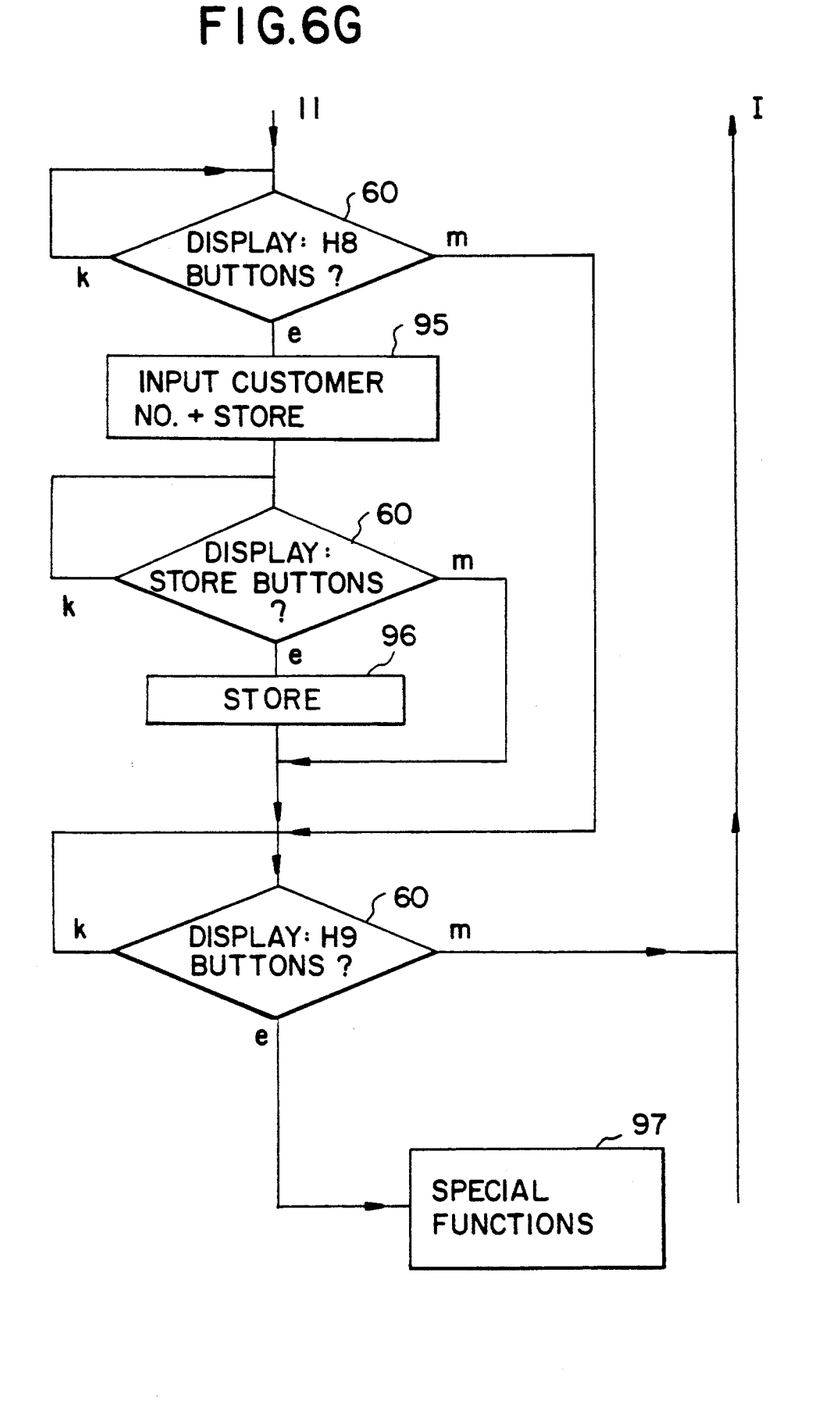

FIG. 5 shows in the form of a flowchart a subroutine for interrogating the push-buttons 4, 5 and 6. The subroutine is called up repeatedly in the flowcharts represented in FIGS. 6A–6G. After the start of the subroutine at A, the button status is read in at a program part 61. After that, the subroutine branches at 62 according to whether the on/off button is depressed. If the button is depressed, the instrument is switched off at 63. If the on/off button 6 is not depressed, the program branches at 64 according to whether the input button 5 is depressed. If d pressed, the subroutine is left at E, if not it is asked in a further branch 65 whether the menu button 4 is depressed. If depressed, the subroutine is left at M; otherwise, the subroutine ends at K.

The subroutine represented in FIG. 5 is provided in FIG. 6 with the reference numeral 60, although for the sake of clarity the exit of the subroutine, which has a switching-off of the instrument as a consequence, is not shown. The parts of the flowcharts of FIGS. 6A–6G belong together as labelled by the letters A to R.

In the program represented by FIG. 6, after the switching-on at 71, it is first of all tested at 72 whether the instrument has beforehand been in operational readiness. If this is not the case, a warming-up phase is carried out at 73 for a time of 185 s. In program part 74, there follows a scavenging phase of 15 s, in which the pump 47 is put into operation and the then available measurement results of sensors 48 and 49 are set to 20.9% and 0 ppm respectively.

The instrument is now ready for measuring the combustion air temperature with the second temperature sensor 42. This takes place in program part 75. This is followed by a button interrogation 60. As long as no button is depressed, it remains with the display and measurement of the combustion air temperature. If, however, the menu button is depressed, there takes place at 76 a measurement and display of the combustion air temperature by the sensor 41 located in the entry region of the measuring channel 45. If, however, the input button is depressed during the subroutine 60, the value of the combustion air temperature measured at 75 is stored at 77, that is to say it is entered in a read/write memory of the microcomputer 31. If after program part 76 the input button is depressed, the value of the combustion air temperature measured in program part 76 is stored.

If, however, after program part 76 the menu button is depressed, the program is continued with subroutine 60, without storing the combustion air temperature, the line H1 of the main menu 21 being displayed on the liquid-crystal display 52. If the menu button is then depressed once again, data are stored for the fuel last chosen. If, however, in sub-routine 60 the input button is depressed, the subroutine 60 is called up once again, but with line B1 of the fuel selection menu 22 displayed. By actuating the menu button, the subroutine 60 can be repeated with a display of a different line of the fuel selection menu, until the desired fuel has been selected. For the sake of clarity, not all repetitions are shown in FIG. 6. After depressing the input button in the respective run of the subroutine 60, the data of the fuel then selected are taken over into the read/write memory of the microcomputer 31 in one of program parts 79 to 81.

After this fuel selection, line H2 of the main menu 21 is displayed. Consequently, a renewed button input is requested. If the input button is depressed, the boiler temperature is input and stored in program part 82. This is followed by the display of line H3 of the main menu and a renewed button input. If in this case the input button is depressed, three smoke spot numbers can be input with the aid of a submenu (not shown in detail) in program part 83 and the question answered whether oil derivatives are to be taken into consideration or not. In this program part, the average smoke spot number is then calculated and stored.

This is followed in subroutine 60 by the display of line H4 of the main menu and a button input, which in this case can only comprise actuation of the input button. This is followed by the measuring operation and evaluation of the measured variables and display of the oxygen content, the carbon monoxide content and the unrarefied carbon monoxide content in program part 84. In a following button input, it is then decided whether lambda (air rates) is to be calculated. If this is the case, the values for lambda, oxygen and carbon monoxide are stored in program part 85.

Thereafter, line H5 of the main menu is displayed and a button input awaited. If the input button is actuated, measurement and calculation are carried out once again in program part 86 and the values for oxygen, carbon dioxide and the waste gas temperature are displayed. After renewed actuation of the input button, $q_A$ is calculated in program part 87 and is stored in addition to the values mentioned above.

In the program parts which follow, a measurement of the stack draft is performed if after display of line H6 of the main menu the input button is depressed. After an actuation of the input button in subroutine 60, the draft is set to 0 at 88. Thereafter, the input button has to be actuated again, whereupon the draft is measured and displayed in program part 89. Following actuation of the input button once again, the representative vacuum in the stack draft is stored at 90. (See FIG. 5)

The program parts which follow serve to display the parameters used in the measurements performed up to then as well as measured and calculated values if after display of line H6 of the main menu the input button is depressed. In this case, some of these particulars are respectively displayed in program parts 91 to 94 and, in between, with the aid of subroutine 60, the user is given the opportunity either to have the next value displayed or to return to the main menu.

Thereafter, in a subroutine 60, line H8 of the main menu is displayed, in which input of the customer number is requested. If this is to be carried out, after actuating the input button a program 95 is called up, in which, again in the form of a submenu, a figure is selected each time on the basis of decimal places with the aid of the menu button and the input button. Thereafter, it is asked with the aid of the subroutine 60 whether the measured data are to be stored for the customer number chosen at 95. If this is so, storage takes place in program part 96.

After that, subroutine 60 is again called up and menu line H9 displayed, which states whether a special function menu 23 is to be activated. If this is not the case, after actuation of the menu button, the program returns to the display of line H1 of the main menu. Otherwise, a program 97 with special functions is called up, which provides various other functions, for example transferring the stored data via the V24 interface and possibilities of managing the stored data.

What is claimed is:

1. A compact measuring instrument for measuring waste from heating installations, comprising at least one sensor and pump arranged in a measuring channel, a microcomputer for controlling the measuring sequence and for processing sensor signals, and connected to the microcomputer an alphanumeric display device and two control elements, wherein one control element serves to page in a selection menu by which one menu item is displayed on the display device, and wherein the other control element serves to input the menu item displayed, said compact measuring instrument is carried by an operator using only one hand and is easily operated by the same one hand, wherein said control elements comprise push-buttons and wherein an additional push-button is connected to an on/off switch, and wherein each of said push-buttons are arranged in the vicinity of one edge of a front side of the measuring instrument, which side also bears the display device.

2. A measuring instrument as claimed in claim 1, wherein the push-buttons for the control elements are arranged closer together than the distance between the on/off push-button and the closest control element push-button.

3. A measuring instrument as claimed in claim 2, wherein the push-buttons for the control element are arranged within a depression.

4. A measuring instrument as claimed in claim 1, wherein a sequence of inputs and measurements to be performed by an operator is predetermined according to a program provided for the microcomputer.

5. A measuring instrument as claimed in claim 1, wherein said at least one sensor comprises a pressure sensor.

6. A measuring instrument as claimed in claim 5, wherein the pressure sensor is calibrated to 0 hPa before pressure measurement.

7. A measuring instrument as claimed in claim 1, wherein said at least one sensor comprises a temperature sensor.

8. A measuring instrument as claimed in claim 1, additionally comprising an intake opening and an outlet opening of the measuring channel, whereby at least the intake opening is arranged on a side of the measuring instrument furthest from the control elements.

9. A measuring instrument as claimed in claim 8, additionally comprising a probe line connected to the intake opening.

10. A measuring instrument as claimed in claim 1, wherein flexible magnets are arranged on a rear side of the instrument.

11. A measuring instrument as claimed in claim 1, additionally comprising a connector for transferring data.

12. A measuring instrument as claimed in claim 1, wherein said at least one sensor comprises an oxygen sensor and a CO sensor.

13. A measuring instrument as claimed in claim 12, wherein said at least one sensor additionally comprises a temperature sensor and pressure sensor.

14. A measuring instrument as claimed in claim 1, wherein said at least one sensor comprises at least two temperature sensors.

15. A compact measuring instrument for measuring waste from heating installations, comprising at least one sensor and pump arranged in a measuring channel, a microcomputer for controlling the measuring sequence and for processing sensor signals, and connected to the microcomputer an alphanumeric display device and two control elements, wherein one control element serves to page in a selection menu by which one menu item is displayed on the display device, and wherein the other control element serves to input the menu item displayed, wherein after switching-on the instrument, an oxygen measuring device present in the measuring instrument is calibrated to 20.9% by volume and a CO measuring device present in the measuring instrument is calibrated to 0 by said microcomputer.

* * * * *